(12) United States Patent
Kaufmann et al.

(10) Patent No.: US 7,759,947 B2
(45) Date of Patent: Jul. 20, 2010

(54) METHOD AND APPARATUS FOR DETERMINING THE MOISTURE OF A RUNNING MATERIAL WEB

(75) Inventors: Oliver Kaufmann, Heidenheim (DE); Peter Biener, Herbrechtingen (DE); Rainer Wenzl, Riesburg (DE)

(73) Assignee: VOITH Patent GmbH, Heidenheim (DE)

(*) Notice: Subject to any disclaimer, the term of this patent is extended or adjusted under 35 U.S.C. 154(b) by 268 days.

(21) Appl. No.: 11/957,000

(22) Filed: Dec. 14, 2007

(65) Prior Publication Data

US 2008/0211514 A1    Sep. 4, 2008

(30) Foreign Application Priority Data

Dec. 15, 2006  (DE)  ........................ 10 2006 059 308

(51) Int. Cl.
*G01R 27/04*  (2006.01)
(52) U.S. Cl. .............................. 324/643; 73/73; 73/579; 73/865.9
(58) Field of Classification Search .................. 324/643
See application file for complete search history.

(56) References Cited

U.S. PATENT DOCUMENTS

| | | | |
|---|---|---|---|
| 5,500,599 A | | 3/1996 | Stange |
| 5,826,458 A | * | 10/1998 | Little ............................ 73/73 |
| 6,099,690 A | | 8/2000 | Hu et al. ...................... 162/198 |
| 2004/0261550 A1 | * | 12/2004 | Asa ............................. 73/865.9 |
| 2006/0028213 A1 | * | 2/2006 | Typpo et al. ................. 324/640 |
| 2006/0288782 A1 | * | 12/2006 | Sawamoto et al. ............ 73/579 |
| 2007/0018657 A1 | | 1/2007 | Nagata et al. |
| 2008/0249730 A1 | | 10/2008 | Svensson et al. |

FOREIGN PATENT DOCUMENTS

| | | |
|---|---|---|
| EP | 0292571 | 12/1987 |
| EP | 0 292 571 A1 * | 11/1988 |
| EP | 0468023 | 2/1991 |
| EP | 0 758 085 A2 | 12/1997 |
| EP | 1000314 | 7/1998 |
| EP | 1331476 B1 | 7/2003 |
| WO | WO 00/04375 | 1/2000 |

\* cited by examiner

*Primary Examiner*—Timothy J Dole
*Assistant Examiner*—Benjamin M Baldridge
(74) *Attorney, Agent, or Firm*—Taylor & Aust, P.C.

(57) ABSTRACT

In a method for determining the moisture of a running material web, in particular a paper web or paperboard web, the material web is scanned by way of a sensor including a microwave resonator, the resonance response of the microwave resonator is investigated, and the moisture in the material web is established in the light of this resonance response while taking account of the distance between the microwave resonator and the material web. Also disclosed is a corresponding apparatus for determining the moisture.

40 Claims, 5 Drawing Sheets

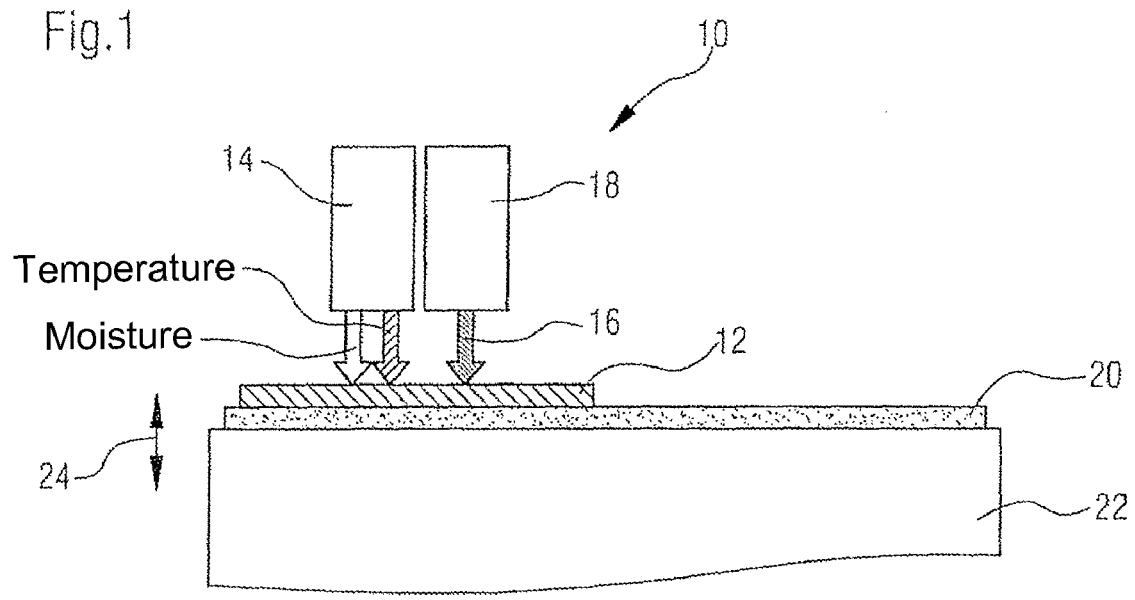
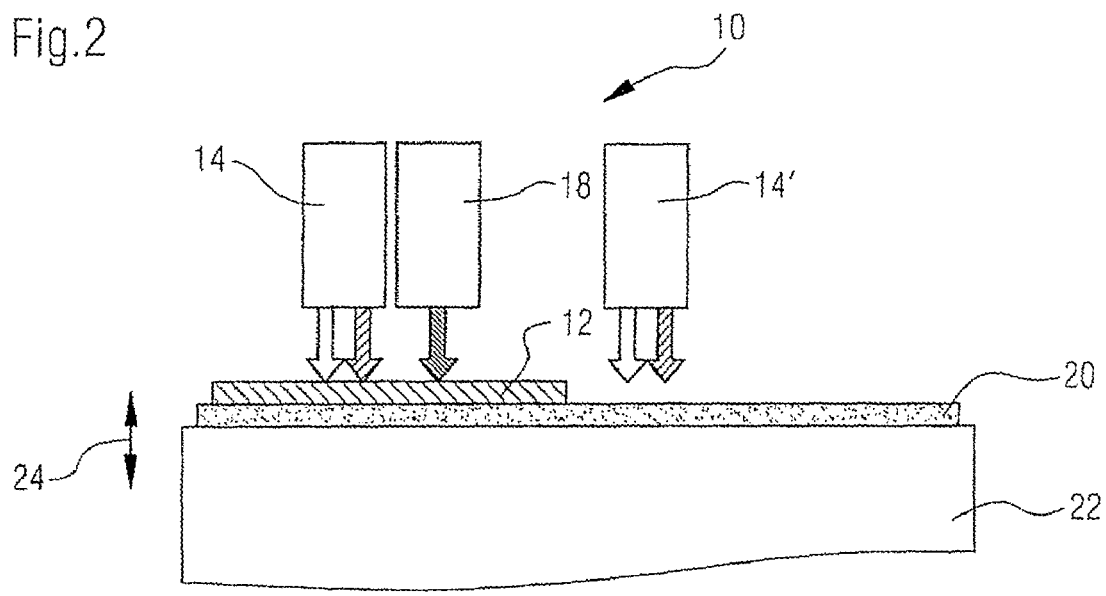

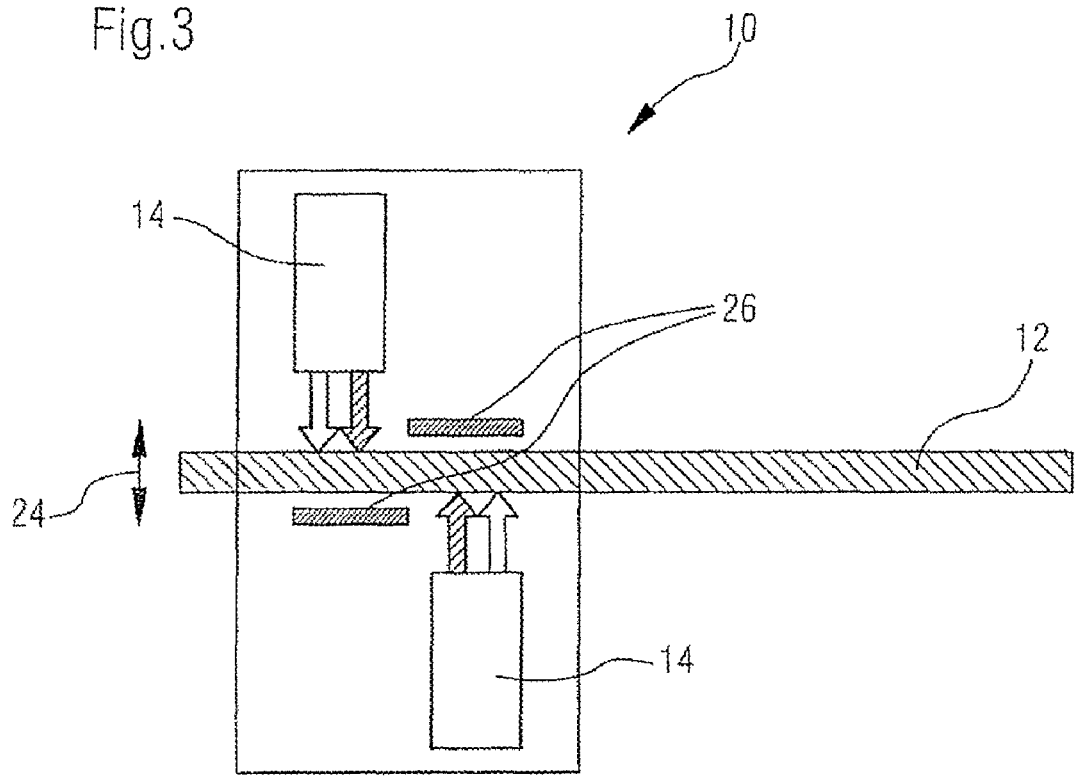
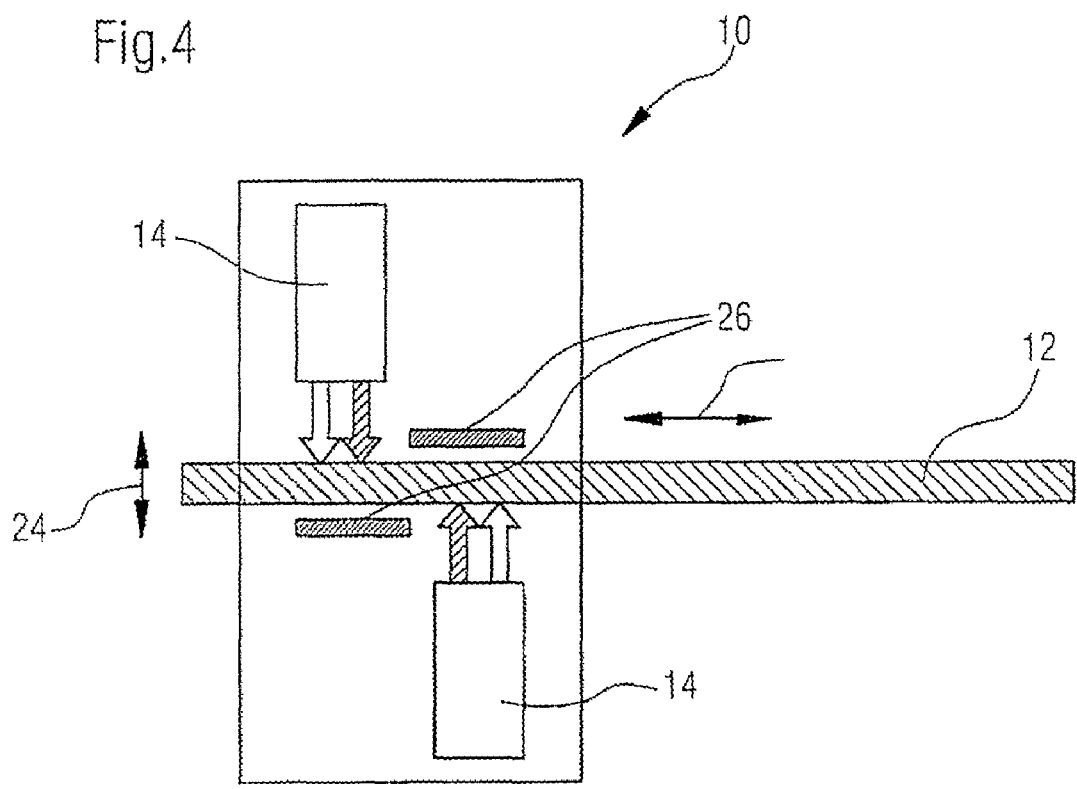

METHOD AND APPARATUS FOR DETERMINING THE MOISTURE OF A RUNNING MATERIAL WEB

BACKGROUND OF THE INVENTION

1. Field of the Invention

This invention relates to a method and an apparatus for determining the moisture of a running material web, in particular a paper web or paperboard web.

2. Description of the Related Art

The moisture of the running paper web is one of the most important measurement and control variables in the paper production process. For fast control operations, the measured values have to be precisely established online. The measured moisture value can then be used for measurement and control tasks.

Today, moisture is determined in the paper industry usually by optical methods, such as using characteristic wavelengths of water and fibers measured spectroscopically. The percentage of moisture content of the paper is then calculated using the transmission or reflection response. A disadvantage of this method is the high technical outlay, the high price and the large dimensions of the corresponding sensors.

Another technology used in the paper industry for determining moisture is based on an indirect method such as measuring the electrical conductivity of the paper, which stands in correlation to the quantity of water contained in the paper (cf. U.S. Pat. No. 6,099,690). The disadvantages of this known method are that the conductivity depends on the chemical composition of the paper and that the measurement is dependent on the dielectric constant of the paper and on the distance of the sensor element from the paper.

It was already proposed to determine the microwave resonance frequency of a cavity resonator implemented in a sensor as a way of measuring the moisture. The resonance response of such a cavity resonator changes with the moisture of the paper. The disadvantage of this method is, among other things, that the sensor has relatively large dimensions.

Several developments and advances in microwave technology for the communications industry in the frequency range important for moisture measurement, namely 1 to 100 GHz, have resulted in a miniaturization of the corresponding components and a drop in their prices. New avenues for further development have thus opened. Described in EP 1 000 314 B1 is an open cavity sensor for distance measurement.

SUMMARY OF THE INVENTION

The object of the present invention is to create an improved method and an improved apparatus which enable, in as simple and economical a manner as possible, the reliable determination of the moisture or weight of water in the running material web. The present invention is more economical and more reliable than the usual expensive optical methods and apparatuses used to date.

The present invention includes a method for determining the moisture of a running material web, in particular a paper web or paperboard web, with which the material web is scanned by way of a sensor including a microwave resonator, the resonance response of the microwave resonator is investigated, and the moisture in the material web is determined in the light of this resonance response while taking account of the distance between the microwave resonator and the material web.

As the result, it is now possible to reliably determine the weight of water in a running material web, in particular a paper web or paperboard web, independently of the distance of the sensor from the material web. With the inventive method an economical and reliable alternative to the usual expensive optical methods used hitherto is provided. The microwave resonator used in this case is characterized, among other things, by low costs, small dimensions and the fact that there is no dependence on temperature due to the sensor.

Hence the measurement principle typical for a microwave resonator, namely measuring the resonance frequency of certain select modes, can be used also for measuring the moisture. If the distance of the sensor from the material web is held constant, for example, or is simultaneously established by way of an additional sensor, for example, such that the distance is exactly known, then the dependence on distance of the measurement taken by the microwave resonator can be compensated without difficulty.

The inventive method is used for measuring the moisture in paper, for controlling various transverse profiles or for optimizing the dewatering in the paper running direction. Also the method conducts tail measurements in order to optimize the paper transfer by way of a corresponding control system, whereby the moisture value is entered as the actual value into the control circuit in question. The inventive method is also used for measuring the so-called gel point in order to optimize the drying of a coated paper by way of a corresponding drying performance control system. In this case the moisture value is entered as the actual value into the control circuit in question. The moisture correlates with the so-called gel point of the coating, which reflects the fixing or immobilizing of the coating.

Preferably a resonator, in the form of a cavity resonator with a resonator housing is used as the microwave resonator. In this case the cavity resonator can be configured in particular as is described in EP 1 000 314 B1.

Hence the cavity resonator can include a coplanar slot coupling with a coupling line which is terminated on the resonator housing. Alternatively, the cavity resonator can also include a microstrip line for the coupling, which is terminated on the resonator housing. It is also possible moreover for the cavity resonator to be configured as is described in EP 1 000 314 B1.

It is also advantageous, in particular, for the resonance frequency of the microwave resonator to lie in a range of between approximately 1 and 100 GHz for a distance between the microwave resonator and the material web such as exists during the scanning of the material web. Hence for measuring the moisture on a running paper web it is possible to investigate the resonance response of the microwave resonator in a wavelength range from 1 GHz to 100 GHz.

Investigating the resonance response of the microwave resonator entails preferably establishing the position of the minimum/maximum, meaning an extreme value of the resonance curve on the frequency axis and/or determining the width of the resonance curve. Account is thus taken of the fact that the position of the minimum/maximum, meaning an extreme value of the resonance curve, on the frequency axis and the width of said resonance curve or the attenuation depend on the moisture content of the paper.

To ensure an optimal operation of the sensor, the microwave resonator open toward the material web is closed. Advantageously a metallic or dielectric element is positioned a fixed distance from the open or non-metalized or non-dielectric side of the microwave resonator facing the material web.

According to an expedient practical embodiment of the inventive method, the distance between the microwave resonator and the material web is held, at least essentially, constant. The constant distance can then be drawn on for compensating the dependence of the sensor measurement on the distance.

In particular, if provision is made for measuring the material web on one side, use is made, according to an expedient practical embodiment of the present invention of only one sensor with a microwave resonator and the distance between the sensor and the material web is held, at least essentially, constant.

The maximum permissible deviation of the distance from the setpoint distance is preferably <100 μm, and more preferably <10 μm.

According to another expedient embodiment of the present invention it is also possible advantageously to use two sensors provided on the same side of the material web, each sensor having one microwave resonator and each sensor having different sensitivities with regard to the moisture and distance, whereby the moisture is established by way of one of the two sensors and the distance from the microwave resonator to the material web is simultaneously established by way of the other sensor. The different sensitivities are based on different measuring frequencies. Preferably the two sensors are positioned directly adjacent each other.

The distance between a respective sensor and the material web is a maximum of 200 mm, whereby it lies preferably in a range from approximately 1 mm to approximately 10 mm.

Regardless of whether use is made of only one or several sensors, each includes one microwave resonator, the temperature is advantageously measured simultaneously. Account can thus be taken of the fact that the dielectric constant of water changes with the temperature. Preferably the temperature of the material web is measured without contact.

The unit comprising the microwave resonator and the material web is terminated expediently by a metallic supporting surface such as the metallic core of a drum over which the material web is passed. It is possible to provide a skin, in particular a mesh, between the material web and the supporting surface.

To be able to take a calibration measurement without a material web, provision is made for at least one additional sensor with a microwave resonator so that a supporting surface or roller or skin is scanned at a point no longer touched by the material web, as the result of which the measurement accuracy is increased accordingly. It is thus possible to compensate for soiling of the supporting surface or drum or skin formed, for example, by a mesh.

In this case it is an advantage for the additional sensor to be aligned, looking transverse to the web running direction, at least essentially with a sensor scanning the material web.

If measuring is to be performed from two sides, then at least one sensor having a microwave resonator is used advantageously on a free draw of the material web, where the web is not supported, on either of the two opposite sides of the material web. In this case it is an advantage if the sensors provided on opposite sides of the material web are offset from each other, looking in the web running direction, far enough for their respective electromagnetic fields not to interfere with each other. Hence the two sensors should not be arranged directly above each other if at all possible.

In this case too, a unit having respectively one microwave resonator open toward the material web is again expediently terminated. For this purpose it is again possible for a metallic or dielectric element to be positioned a fixed distance from the open or non-metalized or non-dielectric side of the respective microwave resonator facing the material web.

An adjustment of the sensor characteristic curve and/or a calibration of the sensor values with regard to the absolute moisture is carried out.

To establish the moisture content expressed in percent moisture of total mass it is possible to measure the grams per square meter (gsm) of a substance of the material web. The moisture content is the usual pertinent variable in the paper industry.

It is an advantage for the moisture measurement to be performed, looking in the web running direction, a distance from the sensor, used for determining the moisture, in which the moisture of the material web compared to the moisture of the material web in the region of the sensor used for determining the moisture, does not essentially change or the change of moisture is known.

In addition, the present invention is directed to an apparatus for determining the moisture of a running material web, in particular a paper web or paperboard web, having a sensor including a microwave resonator for scanning the material web and an electronic analyzer for investigating the resonance response of the microwave resonator and for determining the moisture in the material web in the light of the resonance response while taking account of the distance between the microwave resonator and the material web.

The apparatus is provided in particular for performing the method according to the invention. The inventive method and the inventive apparatus can be used advantageously in particular for establishing the moisture of a paper edge strip in order to optimize the transfer of a paper web from one region of a paper machine onto another region.

A preferred advantageous application lies therefore in the area of so-called tail measurements, whereby a moisture measurement of a paper edge strip is carried out in order to optimize the transfer of the paper from one region of the paper machine onto another. In this case the moisture measurement can serve as an actual value in a control circuit with which the paper moisture can be adjusted to an ideal or setpoint value for the transfer. As setpoint variables it is possible to use either paper re-watering actuators for increasing the moisture or steam quantity controllers in the drying sections for both increasing the moisture and drying the paper.

The inventive method and the inventive apparatus can also be used in the finishing of paper such as the coating of paper, and in this case in particular for determining the gel point.

An exemplary preferred application lies accordingly in the gel point measurement area. The paper moisture plays an important role in the finishing of paper such as the coating of paper for example. There is a correlation between the so-called gel point of the coating, which is applied to the paper, and the moisture. In this case the gel point defines when the coating is fixed and, accordingly, when the coating process has ended, which is of decisive importance for the follow-up drying groups.

The inventive method and the inventive apparatus can also be used for controlling the transverse and/or longitudinal moisture profile.

Hence a preferred application also lies in the moisture measurement area in general and in the related control of the transverse and longitudinal profile. Various transverse profile control operations can be performed with the sensor measured values thus obtained. A decisive advantage of the microwave resonator used lies in its small size and the low manufacturing costs, as the result of which it is possible to manufacture a sensor strip scanning the entire paper web width. The advantages compared to conventional traversing sensor units are on the one hand that the moisture of the entire paper web width can be established in one go and on the other hand that 100% of the paper web can be measured. By contrast, the conventional traversing measuring units only ever measure a section or a diagonal strip of the paper web width. In principle it is also possible, for cost or compatibility reasons, for the inventively used sensor to be installed in a traversing measuring apparatus.

BRIEF DESCRIPTION OF THE DRAWINGS

The above-mentioned and other features and advantages of this invention, and the manner of attaining them, will become more apparent and the invention will be better understood by reference to the following description of (an) embodiment(s) of the invention taken in conjunction with the accompanying drawing(s), wherein:

FIG. 1 shows a schematic representation of an exemplary embodiment of an apparatus for determining the moisture of a running material web of the present invention, the apparatus being designed for one-sided measurement using two sensors provided on one side of the material web for measuring the moisture and distance respectively;

FIG. 2 shows an embodiment comparable with the embodiment according to FIG. 1, having an additional sensor for a calibration measurement without the material web;

FIG. 3 shows a schematic representation of another embodiment of the apparatus for a two-sided measurement of the present invention, on which at least one sensor is provided respectively on each of the two opposite sides of the material web on a free draw of the material web;

FIG. 4 shows an embodiment of the apparatus comparable with the embodiment according to FIG. 3, whereby in this case however provision is made for a traversing unit comprising the two sensors;

Figure 5:
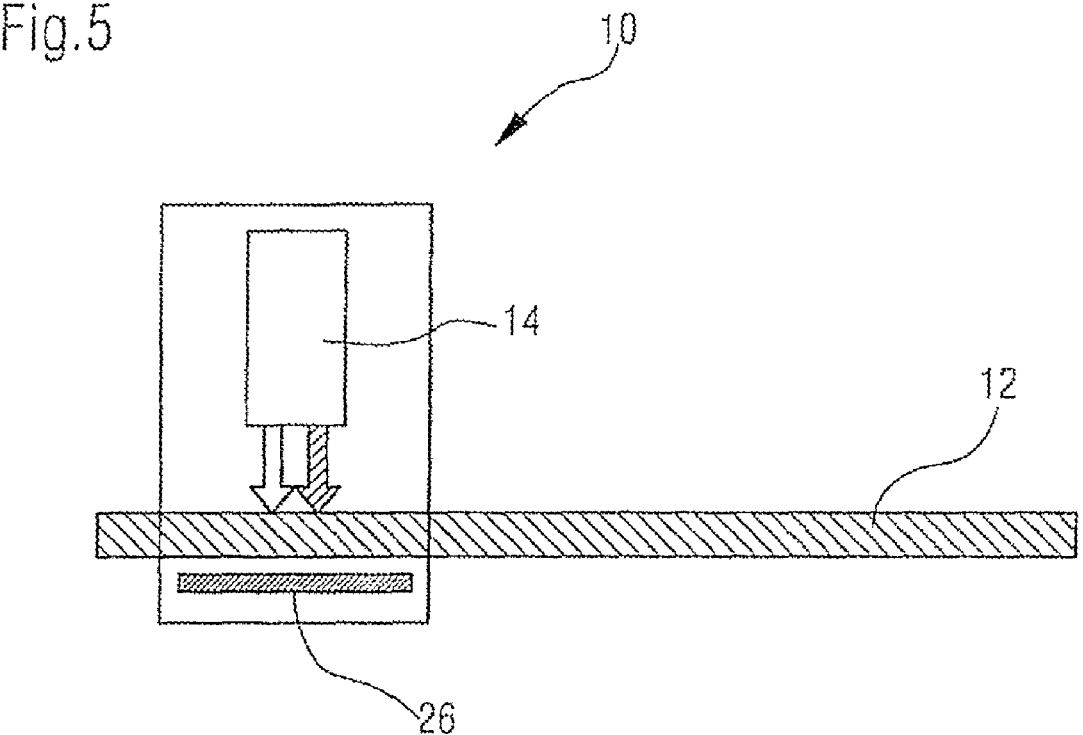
FIG. 5 shows a schematic representation of another embodiment of the apparatus of the present invention having only one sensor arranged a fixed distance from the material web on a free draw of the material web, whereby the unit includes the sensor with the assigned microwave resonator and the material web is terminated by a metallic or dielectric element.

Corresponding reference characters indicate corresponding parts throughout the several views. The exemplification(s) set out herein illustrate(s) (one) embodiment(s) of the invention (, in one form,) and such exemplification(s) (is)(are) not to be construed as limiting the scope of the invention in any manner.

DETAILED DESCRIPTION OF THE INVENTION

Referring now to the drawings, and more particularly to FIG. 1, there is shown a schematic representation of an exemplary embodiment of an apparatus 10 for determining the moisture of a running material web 12 which is a paper web 12.

Apparatus 10 includes a sensor containing a microwave resonator for measuring the moisture of paper web 12 and an electronic analyzer (not shown) for investigating the resonance response of the microwave resonator and for establishing the moisture in paper web 12 in the light of the resonance response while taking account of a distance 16 between the microwave resonator and paper web 12. Sensor 14 includes a device for simultaneous, preferably non-contacting measurement of the temperature of paper web 12.

Provided on the same side of paper web 12 is a second sensor 18 including a microwave resonator for measuring the distance from paper web 12. Sensor 18 and its microwave resonator can be the same distance 16 from paper web 12 as sensor 14 or the microwave resonator assigned thereto can be positioned such that the distance of sensor 14 and its microwave resonator from paper web 12 is also established with the measured distance value received via sensor 18.

Sensors 14 and 18 are provided on the same side of paper web 12 and each include a microwave resonator respectively having different sensitivities with regard to the moisture and the distance, for example, different measuring frequencies. In this case, as already mentioned, the distance from paper web 12 is simultaneously measured by way of second sensor 18.

In the case under discussion, a one-sided measurement is performed. On the side opposite sensors 14 and 18, paper web 12 is supported on a skin 20 in this case, for example, a mesh 20 which is passed over a roller 22 equipped with the skin in question.

The microwave resonators of sensors 14 and 18 are open respectively to paper web 12. Hence they each have a non-metalized and non-dielectric side facing paper web 12. In the case under discussion, the units formed by a respective sensor 14 and 18 and respective microwave resonator and paper web 12 are terminated by a metallic core of roller 22.

After the distance from a respective microwave resonator to paper web 12 is known, it is possible to compensate the dependence on the microwave resonators on the distance in particular by way of an electronic analyzer. A respective change of distance 24 is recorded by way of sensor 18. The maximum changes of distance are expediently <100 μm and preferably <10 μm.

The two sensors 14 and 18 are positioned, looking transverse to the web running direction, directly adjacent each other. The distance to paper web 12 to be investigated can amount in this case to up to 200 mm, whereby it lies preferably in a range from approximately 1 mm to approximately 10 mm.

Because the temperature of the paper web is also measured simultaneously by sensor 14, account can also be taken of the fact that the dielectric constant of water changes with the temperature.

FIG. 2 shows an embodiment comparable with the embodiment according to FIG. 1, having an additional sensor 14' having a microwave resonator for a calibration measurement without paper web 12. It is thus possible for example to compensate accordingly the soiling of mesh 20 by measurement and in particular by way of the electronic analyzer. Additional sensor 14' should be aligned, looking transverse to the web running direction, at least essentially, with sensor 14 provided for measuring the moisture.

FIG. 3 shows a schematic representation of another embodiment of apparatus 10 for a two-sided measurement, on which one sensor 14 includes a microwave resonator for measuring the moisture is provided respectively on each of the two opposite sides of paper web 12 on a free draw of paper web 12. Again the temperature of paper web 12 is also measured simultaneously by way of sensors 14. Each of the units include a respective sensor 14 with a respective microwave resonator and paper web 12 is terminated in this case by a metallic or dielectric element which in the case under discussion is formed respectively by a corresponding termination plate 26, which in this case is metal.

FIG. 4 shows an embodiment of apparatus 10 comparable with the embodiment according to FIG. 3, whereby in this case however provision is made for a traversing unit including sensors 14 and termination plates 26.

FIG. 5 shows in a schematic representation another embodiment of apparatus 10 having only one sensor 14 having a microwave resonator and being arranged a fixed distance from paper web 12 on a free draw of paper web 12. The unit includes the sensor 14 with the assigned microwave resonator and paper web 12 is terminated by a metallic or dielectric element, in this case a termination plate 26 made preferably of metal.

Figure 6:
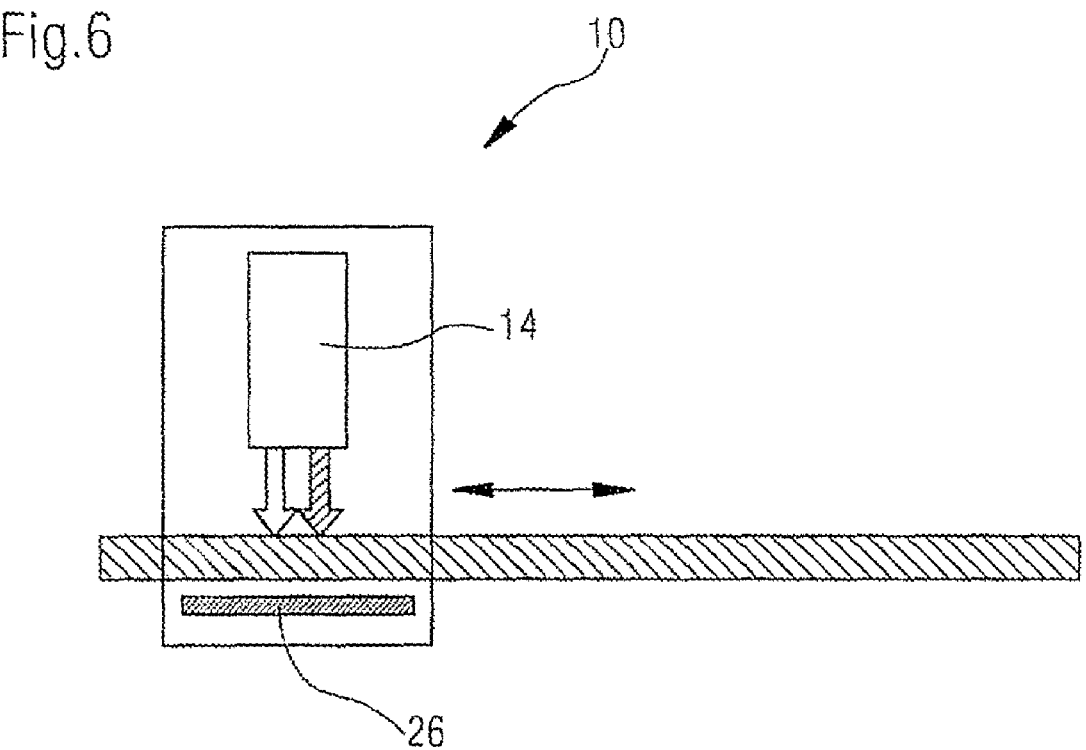
FIG. 6 shows an embodiment of the apparatus comparable with the embodiment according to FIG. 5, whereby in this case however provision is made for a traversing unit including the sensor and the metallic or dielectric element.

FIG. 6 shows an embodiment of apparatus 10 comparable with the embodiment according to FIG. 5, whereby in this case however provision is made for a traversing unit having sensor 14 with its microwave resonator and termination plate 26. As before, sensors 14 of the embodiments presented in FIG. 5 and FIG. 6 again serve respectively to measure the moisture and to measure the temperature.

Figure 7:
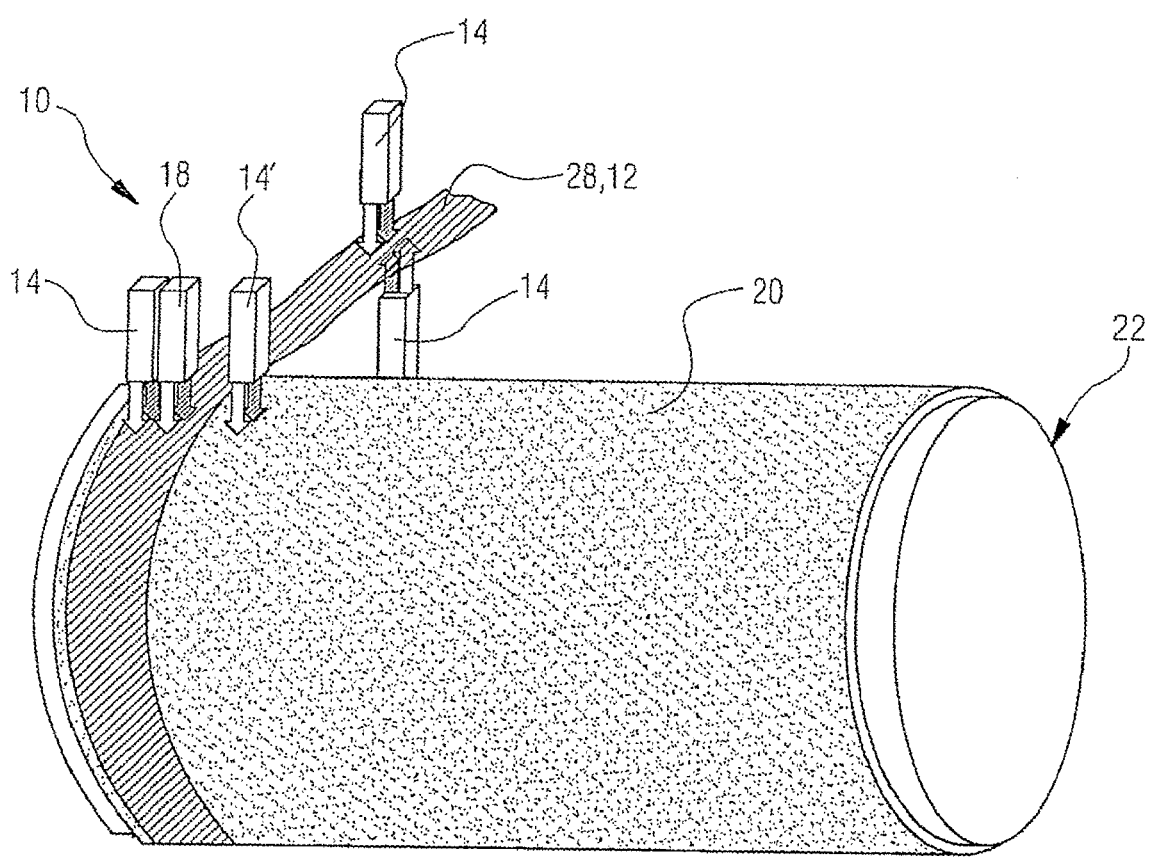
FIG. 7 shows a schematic representation of another embodiment of the apparatus of the present invention which is used for tail measuring.

FIG. 7 shows in a schematic representation another embodiment of apparatus 10 which used for tail measuring. As is evident from FIG. 7, two sensors 14 and 18 include respectively a microwave resonator for measuring the moisture, temperature and distance and being provided on the side facing away from roller 22 are again assigned to the tail or paper edge strip 28 of paper web 12 in the region in which the tail or strip is passed over roller 22 equipped with skin 20 in order to perform initially a one-sided measurement. Also, an additional sensor 14' is provided for a calibration measurement without paper web 12. Hence for this one-sided measurement, a sensor arrangement comparable with the sensor arrangement according to FIG. 2 is provided.

In addition, provision is made on a free draw of the paper edge strip 28 of paper web 12 for respectively an additional sensor 14 including a microwave resonator on each of the two opposite sides of paper wedge strip 28 in order to carry out a two-sided measurement. Hence for this two-sided measurement, a sensor arrangement comparable with the sensor arrangement according to FIG. 3 is provided.

Figure 8:
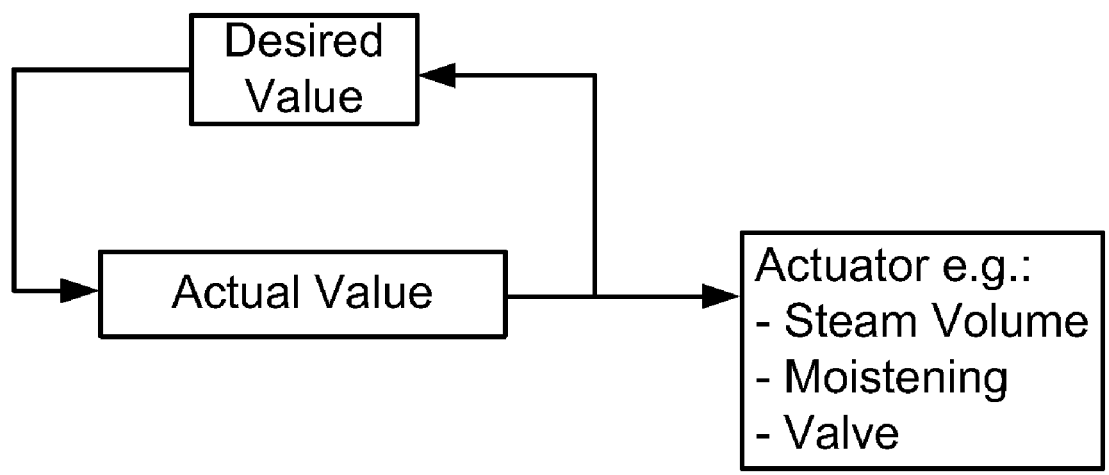
FIG. 8 shows a schematic representation of a control circuit for optimizing the transfer of a paper web on the basis of a tail measurement.

FIG. 8 shows in a schematic representation an exemplary control circuit for optimizing the transfer of a paper web on the basis of a tail measurement. In this control circuit the moisture measurement serves as the actual value. The paper moisture is set by the control circuit to an ideal or setpoint value for the transfer. As setpoint variables it is possible to use either paper re-watering actuators for increasing the moisture and/or steam quantity controllers in the drying sections for both increasing the moisture and drying the paper.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

10 Apparatus for determining the moisture
12 Material web, paper web or paperboard web
14 Sensor
14' Sensor
16 Distance
18 Sensor
20 Skin, mesh
22 Roller
24 Change of distance
26 Metallic or dielectric element, termination plate
28 Tail, paper edge strip

What is claimed is:

1. A method for determining the moisture of a running material web, the material web being one of a paper web and a paperboard web, comprising the steps of:
    scanning the material web by way of a first sensor, said first sensor including a microwave resonator;
    investigating a resonance response of said microwave resonator; and
    establishing an amount of moisture in the material web dependent upon said resonance response while taking into account a distance between said microwave resonator and the material web; and
    electrically terminating a unit including the microwave resonator and the material web with a metallic supporting surface over which the material web is passed, said metallic supporting surface comprising a metallic core of a drum or a roller.

2. The method of claim 1, wherein said microwave resonator includes a resonator in the form of a cavity resonator with a resonator housing.

3. The method of claim 1, wherein said microwave resonator has a resonance frequency that lies in a range of between approximately 1 GHz to 100 GHz during scanning of the material web.

4. The method of claim 1, wherein said investigating said resonance response step includes at least one of establishing a position of at least one of a minimum and a maximum on a frequency axis and establishing the width of a resonance curve.

5. The method of claim 1, wherein said microwave resonator is open toward the material web, said microwave resonator being part of a unit that is sealed, the material web being guided through the unit.

6. The method of claim 5, wherein one of a metallic and dielectric element is positioned a fixed distance from the open or non-metalized or non-dielectric side of the microwave resonator facing the material web.

7. The method of claim 1, wherein said distance between said microwave resonator and the material web is held substantially constant.

8. The method of claim 1, wherein only one sensor including a microwave resonator is used and said distance between said sensor and the material web is held substantially constant.

9. The method of claim 8, wherein a maximum permissible deviation of said distance from a setpoint distance is <100 μm.

10. The method of claim 9, wherein said maximum permissible deviation is <10 μm.

11. The method of claim 1, wherein said scanning step includes using a second sensor provided on the same side of the material web as said first sensor, said second sensor including a microwave resonator, said microwave resonator of said first sensor and said microwave resonator of said second sensor having different sensitivities with regard to moisture and distance, a moisture measurement being established by said first sensor and said distance from the microwave resonator to the material web is simultaneously established by said second sensor.

12. The method of claim 11, wherein said first sensor and said second sensor are positioned directly adjacent each other.

13. The method of claim 11, wherein said distance between at least one of said first sensor and said second sensor and the material web is no more than 200 mm.

14. The method of claim 13, wherein said distance lies in a range from approximately 1 mm to approximately 10 mm.

15. The method of claim 13, further comprising second sensor substantially similar to said first sensor, said first sensor and said second sensor positioned on opposite sides of the material web and offset from each other by a distance in the web running direction, said distance being at least far enough for their electromagnetic fields not to interfere with each other.

16. The method of claim 11, wherein a temperature of the material web is measured simultaneously with said moisture measurement.

17. The method of claim 16, wherein the temperature of the material web is measured without contact of said second sensor with the material web.

18. The method of claim 1, further comprising a step of adjusting at least one of a sensor characteristic curve and a calibration of sensor values responsive to an absolute moisture value.

19. The method of claim 18, further comprising a step of establishing a moisture content of the material web expressed in a percent moisture of total mass, and a step of performing a grams per square meter (gsm) substance measurement of the material web.

20. The method of claim 19, wherein said gsm substance measurement is performed in the web running direction, the material web at a distance from the sensor transverse to the web running direction has a moisture content that when compared to the moisture of the material web in the region of the sensor is one of substantially the same and has a known difference.

21. A method for determining the moisture of a running material web, the material web being one of a paper web and a paperboard web, comprising the steps of:
scanning the material web by way of a first sensor, said first sensor including a microwave resonator;
investigating a resonance response of said microwave resonator;
establishing an amount of moisture in the material web dependent upon said resonance response while taking into account a distance between said microwave resonator and the material web;
electrically terminating a unit including the microwave resonator and the material web with a metallic supporting surface over which the material web is passed, said metallic supporting surface comprising a metallic core of a drum or a roller; and wherein a skin is provided between the material web and said supporting surface.

22. The method of claim 21, wherein said skin is a mesh.

23. The method of claim 21, further comprising a step of taking a calibration measurement without the material web using at least one additional sensor, said at least one additional sensor including a microwave resonator so that at least one of said supporting surface and said skin is scanned at a point no longer touched by the material web.

24. The method of claim 23, wherein said additional sensor is aligned transversely to the web running direction with said first sensor, said first sensor scanning the material web.

25. The method of claim 1, wherein said first sensor is used on either of the two opposite sides of the material web on a free draw of the material web.

26. An apparatus for determining the moisture of a running material web in a paper machine, the material web being one of a paper web and a paperboard web, the apparatus comprising:
a first sensor having a microwave resonator for scanning the material web;
an electronic analyzer for investigating a resonance response of said microwave resonator and for establishing a moisture content of the material web as a function of said resonance response while taking account of a distance between said microwave resonator and the material web; and
a unit including the microwave resonator and the material web is electrically terminated by a metallic supporting surface over which the material web is passed, wherein said metallic supporting surface is a metallic core of a drum or a roller.

27. The apparatus of claim 26, wherein said microwave resonator is in the form of a cavity resonator with a resonator housing.

28. The apparatus of claim 26, wherein said microwave resonator has a resonance frequency that lies in a range of between approximately 1 GHz to 100 GHz for said distance between said microwave resonator and the material web during scanning of the material web.

29. The apparatus of claim according to claim 26, wherein said microwave resonator is open toward the material web, said microwave resonator being part of a unit that is sealed, the material web being guided through the unit.

30. The apparatus of claim 29, wherein one of a metallic and dielectric element is positioned a fixed distance from the open or non-metalized or non-dielectric side of the microwave resonator facing the material web.

31. The apparatus of claim 29, wherein said distance between said microwave resonator and the material web is held substantially constant.

32. The apparatus of claim 29, further comprising a second sensor positioned on the same side of the material web as said first sensor, said second sensor including a microwave resonator, said microwave resonator of said first sensor and said microwave resonator of said second sensor having different sensitivities with regard to moisture and distance, a moisture measurement being established by said first sensor and said distance from the microwave resonator to the material web is simultaneously established by said second sensor.

33. The apparatus of claim 32, wherein said sensor takes a non-contacting measurement of the temperature of the material web, said non-contacting measurement being taken simultaneously with said moisture measurement.

34. The apparatus of claim 26, wherein a skin is provided between the material web and said supporting surface.

35. The apparatus of claim 34, wherein said skin is a mesh.

36. The apparatus of claim 26, further comprising a second sensor having a microwave resonator being positioned on a side of the material web opposite to the positioning of said first sensor, said first sensor and said second sensor being associated with a free draw of the material web.

37. The apparatus of claim 36, wherein said first sensor and said second sensor are offset from each other in the web running direction, at least far enough for their electromagnetic fields not to interfere with each other.

38. The apparatus of claim 26, wherein said electronic analyzer establishes the moisture content of a paper edge strip to thereby optimize a transfer of the paper web from one region of the paper machine onto another region of the paper machine.

39. The apparatus of claim 26, wherein said electronic analyzer is configured for determining a gel point of a coating on the material web.

40. The apparatus of claim 26, further comprising a control system to control at least one of a transverse moisture profile and a longitudinal moisture profile.

* * * * *

UNITED STATES PATENT AND TRADEMARK OFFICE
CERTIFICATE OF CORRECTION

| | | |
|---|---|---|
| PATENT NO. | : 7,759,947 B2 | Page 1 of 1 |
| APPLICATION NO. | : 11/957000 | |
| DATED | : July 20, 2010 | |
| INVENTOR(S) | : Oliver Kaufmann et al. | |

It is certified that error appears in the above-identified patent and that said Letters Patent is hereby corrected as shown below:

COLUMN 10

At line 35, please delete "29", and substitute therefore --26--; and

At line 38, please delete "29", and substitute therefore --26--.

Signed and Sealed this

Fourth Day of October, 2011

David J. Kappos
*Director of the United States Patent and Trademark Office*